(12) United States Patent
Ankenbauer et al.

(10) Patent No.: US 8,119,353 B2
(45) Date of Patent: Feb. 21, 2012

(54) RAPID ONE-STEP REVERSE TRANSCRIPTASE PCR

(75) Inventors: Waltraud Ankenbauer, Penzberg (DE); Ursula Grepl, Grafelfing (DE); Rita Haerteis, Ried-Kochel a. S. (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 274 days.

(21) Appl. No.: 12/061,700

(22) Filed: Apr. 3, 2008

(65) Prior Publication Data

US 2008/0248535 A1    Oct. 9, 2008

(30) Foreign Application Priority Data

Apr. 5, 2007 (EP) .................................... 07007173

(51) Int. Cl.
*C12Q 1/68* (2006.01)
*C12P 19/34* (2006.01)
(52) U.S. Cl. .................... 435/6.12; 435/91.2; 435/91.51
(58) Field of Classification Search ............. 435/6, 91.2, 435/91.51, 6.12
See application file for complete search history.

(56) References Cited

U.S. PATENT DOCUMENTS

| | | | |
|---|---|---|---|
| 5,118,801 A | 6/1992 | Lizardi et al. | |
| 5,210,015 A | 5/1993 | Gelfand et al. | |
| 5,487,972 A | 1/1996 | Gelfand et al. | |
| 5,538,848 A | 7/1996 | Livak et al. | |
| 5,561,058 A | 10/1996 | Gelfand et al. | |
| 5,624,833 A | 4/1997 | Gelfand et al. | |
| 5,674,738 A | 10/1997 | Abramson et al. | |
| 5,804,375 A | 9/1998 | Gelfand et al. | |
| 5,876,924 A * | 3/1999 | Zhang et al. ...................... | 435/6 |
| 6,174,670 B1 | 1/2001 | Wittwer et al. | |
| 2003/0108898 A1 * | 6/2003 | Choppa ............................ | 435/6 |

FOREIGN PATENT DOCUMENTS

| | | |
|---|---|---|
| EP | 1152062 A2 | 11/2001 |
| WO | 91/09944 A2 | 7/1991 |
| WO | 94/08032 A1 | 4/1994 |
| WO | 97/46707 A2 | 12/1997 |
| WO | 97/46712 A2 | 12/1997 |
| WO | 97/46714 A1 | 12/1997 |

OTHER PUBLICATIONS

Baltimore, D., Nature, "Integrated Amplification and Detection of the C677T Point Mutation in the Methylenetetrahydrofolate Reductase Gene by Flourescence Resonance Energy Transfer and Probe Melting Curves," 226, 1209-1211 (1998).
Golomb, M. et al., "Endonuclease Activity of Purified RNA-directed DNA Polymerase from Avian Myeloblastosis Virus," The Journal of Biological Chemistry, 245:5, 1606-1613 (Mar. 10, 1979).
Langmann, T. et al.,"Real-Time Revers Transcription-PCR Expression Profiling of the Complete Human ATP-Binding Cassette Transporter Superfamily in Various Tissues," Clinical Chemistry, 49:2, 230-238 (2003).
Matthews, J. et al., Analytical Strategies for the Use of DNA Probes, Analytical Biochemistry 169, 1-25 (1988).
Myers, T. et al., "Reverse Transcription and DNA Amplification by a Thermus thermophilus DNA Polymerase," Biochemistry, 30:31, 7661-7666.
Temin, H. et al., "RNA-dependent DNA Polymerase in Virions of Rous Sarcoma Virus," Nature 226, 1211-1213 (Jun. 27, 1970).
SuperScript III Platinum One-Step Quantitative RT-PCR System. Invitrogen Technical Notes, Sep. 16, 2005.
Quantitect Probe RT-PCR Handbood, Qiagen, Aug. 2003, pp. 17, 19, 22.

* cited by examiner

*Primary Examiner* — Kenneth R. Horlick
*Assistant Examiner* — Joyce Tung (57) ABSTRACT

The present invention is directed to a method for performing a one-step RT-PCR for amplifying a target RNA comprising the steps (i) providing a sample which is supposed to contain said target RNA (ii) adding a reaction mixture comprising all reagents necessary to reverse transcribe said target RNA into cDNA and amplify at least a portion of said cDNA (iii) incubating said sample for a time interval of 0 seconds to 40 seconds at a temperature between 20° C. and 65° C., and (iv) subjecting said sample to multiple cycles of a thermocycling protocol wherein the temperature of said sample is varied between at least a first temperature between 37° C. and 72° C. and a second temperature between 85° C. and 100° C.

7 Claims, 8 Drawing Sheets

Fig. 1

Reverse transcription for 20 minutes at 25°C

Fig. 2

Reverse transcription for 10 minutes at 25°C

Fig. 3

Reverse transcription for 5 minutes at 25°C

Fig. 4

Reverse transcription for 0 minutes at 25°C

Fig. 5

RNA amplification without incubation to allow reverse transcription

Fig. 6

Reverse transcription at 63°C for 3 seconds

Fig. 7

Reverse transcription for 10 seconds at 63°C

Fig. 8

Reverse transcription at 63°C for 3 minutes

RAPID ONE-STEP REVERSE TRANSCRIPTASE PCR

RELATED APPLICATIONS

This application claims priority to European application EP 07007173.3 filed Apr. 5, 2007.

BACKGROUND OF THE INVENTION

The present invention relates to the field of analyzing mRNA expression by means of performing a reverse transcriptase (RT) reaction and subsequently performing a polymerase chain reaction (PCR) in order to quantify the amount of generated cDNA. More specifically, the present invention relates to an improved method of performing a one-step RT-PCR, characterized in that the time for reverse transcriptase reaction as such is minimized.

BACKGROUND

The discovery of the reverse transcriptases in the seventies disproved the "central dogma" of molecular biology on the information transfer from DNA via RNA to protein as a unidirectional process (Temin. H., and Mizutani, S., Nature 226 (1970) 1211-1213; Baltimore, D., Nature 226 (1970) 1209-1211). The enzymatic characterization of these RNA-dependent DNA polymerases is the basis for current understanding on the amplification cycle of RNA viruses and thus also on the development and spread of diseases that are caused by this type of virus (cancer, AIDS, etc.).

However, reverse transcriptases are also a tool for molecular biologists for the synthesis, amplification, and cloning of cDNAs (RT-PCR). This technology allows a simplified and accelerated examination of gene expression in eukaryotic cells. After isolating the total mRNA from cell extracts or tissues, the mRNA is translated back into cDNA by the reverse transcriptase and amplified by the subsequent PCR step to enable cloning and characterization. Consequently it is not necessary to, on the one hand, elucidate the intron and exon structures of the genes but, on the other hand, it is also possible to examine gene expression in the cell during various life cycles or during the development of diseases (such as cancer).

Reverse transcriptases from three different retroviruses have hitherto been closely examined: The RT from Moloney murine leukemia virus (MMLV). This enzyme consists of a single subunit with a molecular weight of 78 kDa (Prasad, V. R., (1993) reviewed in Reverse Transcriptase, Cold Spring Harbor, N.Y.: Cold Spring Harbor Laboratory Press, 135). In addition, an RT from human immunodeficiency virus (HIV) is known. This RT is a heterodimer that is composed of two subunits p66 and p51, the p51 subunit being formed by proteolytic cleavage of p66 (Le Grice. S. F. J. (1993) reviewed in Reverse Transcriptase, Cold Spring Harbor, N.Y. Cold Spring Harbor Laboratory Press, 163). In addition RTs are known from avian sarcoma leukosis virus (ASLV). The RT obtainable from avian myeloblastosis virus (AMV) also belongs to the ASLV family. This RT is also a heterodimer that is composed of an alpha-chain with a molecular weight of ca. 63 kDa and a beta-chain with a molecular weight of ca. 95 kDa. In this case the alpha-chain is also formed by proteolytic processing of the beta-chain (Golomb, M., and Grandgenett. D. J., Biol. Chem. 254 (1979) 1606-1613; Weiss, R., et al., Molecular Biology of tumor viruses, 2nd edition: RNA tumor viruses 1/text. Cold Spring Harbor Laboratory, Cold Spring Harbor, N.Y. (eds. 1984).

There are also thermostable DNA polymerases Which in addition to their DNA dependent DNA polymerase activity have been disclosed to comprise an RNA-dependent reverse transcriptase activity. Those enzymes are particularly useful for methods of performing a one-step PCR, characterized in that subsequent to a reverse transcription step, the generated cDNA is amplified by means of PCR without intermediate opening of the reaction vessel.

One of the known DNA polymerases having high reverse transcriptase activity is obtainable from *Thermus thermophilus* (Tth polymerase) (WO 91/09944, U.S. Pat. No. 5,561,059). Tth polymerase, as well as Taq polymerase, lacks 3' to 5' exonucleolytic proofreading activity. This 3' to 5' exonuclease activity is generally considered to be desirable because it allows removal of misincorporated or unmatched bases in the newly synthesized nucleic acid sequences. Another thermophilic pol I-type DNA polymerase isolated from *Thermotoga maritime* (Tma pol) has 3' to 5' exonuclease activity. U.S. Pat. No. 5,624,833 provides means for isolating and producing, Tma polymerase. However, both DNA polymerases. Tth as well as Tma polymerase, show reverse transcriptase activity only in the presence of manganese ions.

The DNA polymerase of *Carboxydothermus hydrogenoformans* shows reverse transcription activity in the presence of magnesium ions and in the substantial absence of manganese ions and can be used to reverse transcribe RNA to detect and amplify (in combination with a thermostable DNA polymerase like Taq) specific sequences of RNA. Using DNA polymerase of *Carboxydothermus hydrogenoformans* a high specificity of transcription is observed with short incubation times. A high specificity is observed using, e.g., 5 minutes of incubation time and 33 units of DNA polymerase protein. With longer incubation times, also with lower amounts of *Carboxydothermus hydrogenoformans* polymerase, specific products can be obtained. However an unspecific smear of products is occurring. These unspecific products might be caused by the 5'-3' exonuclease activity of the polymerase which enables the enzyme to cleave the template at secondary structures ("RNaseH"-activity) and to create additional primers which can be elongated by the DNA polymerase activity.

It is also established in the art to provide mixtures of reverse transcriptase enzymes and thermostable DNA polymerases in order to provide a reagent mixture that can be used for performing a 1-step RT-PCR amplification (WO 94/08032). Those mixtures are now commercially available from a variety of suppliers and thus most frequently used in the art. (Qiagen Cat. Nos 210210, 210212), (USB Cat. No. 78350), (Clontech Cat. No. K1403-1), (Invitrogen Cat. Nos 11736-051, 11736-059).

However, all protocols published and recommended so far require a substantial time interval for performing the reverse transcriptase reaction step prior to the PCR thermocycling protocol. The recommended time interval usually is between 30 minutes and 1 hour (Qiagen. Clontech, USB). Five-minute reverse transcriptase reaction steps are disclosed for I-step RT-PCR using *Thermus thermophilus* DNA polymerase (Myers, T. W., and Gelfand, D. H., Biochemistry, 30 (1991)766: 1-7666). A 3-minute reverse transcriptase reaction step is recommended for the Superscript/Platinum enzyme blend from Invitrogen (Cat. Nos 11736-051, 11736-059). In addition, U.S. Pat. No. 5,561,058 discloses a minimal time interval of 1 minute as the required minimal time for performing a reverse transcriptase reaction prior to the PCR thermocycling.

Thus all methods disclosed above require a time consuming step of preincubation at lower temperatures such that the reverse transcriptase reaction step can take place. It was therefore an object of the present invention to provide an improved method of one-step RT-PCR.

SUMMARY OF THE INVENTION

In view of the methods mentioned above, it was very surprising that the reverse transcriptase step can be shortened to very short time intervals, or a preincubation can even completely become omitted. Thus, the present invention is directed to a method for performing a one-step RT-PCR for amplifying a target RNA comprising the steps of
provifing a sample which is supposed to contain said target RNA,
adding a reaction mixture comprising all reagents necessary to reverse transcribe said target RNA into cDNA and amplify at least a portion of said cDNA,
incubating said sample for a time interval of 0 seconds to 40 seconds at a temperature between 20° C. and 65° C., and
subjecting said sample to multiple cycles of a thermocycling protocol wherein the temperature of said sample is varied between at least a first temperature between 90° C. and 100° C. and a second temperature between 50° C. and 75° C.

Preferably, the incubation step can be as short as 20 seconds. More preferably, the incubation step can be less than 5 seconds. Most preferably the incubation step can be 0 seconds, i.e., the incubation step can be omitted completely.

Also preferably, the temperature in the incubation step is between 37° C. and 65° C.; most preferably, said temperature is between 37° C. and 55° C.

In one embodiment, said one-step RT-PCR reaction is catalyzed by a thermostable polymerase comprising DNA dependent polymerase activity and reverse transcriptase activity. For example, said polymerase may be obtainable from the eubacterial genus *Thermus*. In a particular embodiment, said polymerase is obtainable from *Thermus thermophilus*.

Alternatively, said one-step RT-PCR reaction is catalyzed by a mixture of at least a thermostable polymerase comprising DNA dependent polymerase activity and at least a reverse transcriptase.

The present invention is particularity suitable for amplification of cDNA fragments having a size of about 0.2 kb or less.

A further important aspect of the present invention is a method of performing RT-PCR as disclosed above characterized in that the progress of said one-step RT-PCR reaction is monitored in real time.

BRIEF DESCRIPTION OF THE DRAWINGS

FIGS. 1-8 show real-time RT PCR for amplifying ABCC2 RNA using various times and temperatures for preincubation prior to the thermocycling protocol. The left, two curves in each figure always correspond to a sample of 100 pg mRNA. The right two curves in each figure always correspond to a sample of 10 pg mRNA.

DETAILED DESCRIPTION OF THE INVENTION

The present invention provides an improved method for performing a one-step RT-PCR reaction. The improvement is based on the surprising fact that the reverse transcriptase reaction of 1-step RT-PCR is completed after a very short time interval of free incubation at an appropriate temperature in conjunction with the temperature increase for denaturation during the first cycle of the PCR thermocycling protocol. More precisely, the present invention is directed to a method for performing one-step RT-PCR for amplifying a target RNA comprising the steps of
providing a sample which is supposed to contain said target RNA,
adding a reaction mixture comprising all reagents necessary to reverse transcribe said target RNA into single-stranded cDNA and amplify at least a portion of said single-stranded cDNA,
incubating said sample for a time interval of 0 seconds to 40 seconds at a temperature between 20° C. and 65° C., and
subjecting said sample to multiple cycles of a thermocycling protocol, characterized in that temperature of said sample is varied between at least a first temperature between 90° C. and 100° C. and a second temperature between 50° C. and 75° C.

All reagents which are necessary to perform an RT-PCR reaction such as buffers, primers, and deoxynucleotides are well known in the art. Furthermore, an optimization of concentrations used in the context of the present invention can be obtained through routine experiments.

The reverse transcriptase reaction takes place during the incubation step and during the first temperature increase for denaturation of the sample within the thermocycling step. It has been shown by the inventors that the time interval of the incubation step and practice can even be much shorter than 40 seconds.

Preferably it is as short as 20 seconds, and more preferably, it is even short as 5 seconds or less. In a specific embodiment, the time interval for the incubation step is 0 seconds, which means that the incubation step is omitted completely.

In other words, the incubation step of the present invention can also be defined as "optionally" incubating said sample for a time interval of less than 40 seconds, preferably less than 20 seconds, and most preferably less than 5 seconds at the temperature between 20° C. and 65° C.

In case a short incubation step at a temperature between 20° C. and 65° C. according to the invention is being performed, such a preincubation can take place either in a respective thermostated device or alternatively already within a thermocycler instrument that subsequently is being used for performing the PCR thermocycling protocol.

Due to the fact that the incubation step can be omitted completely, it has to be concluded that the reverse transcriptase reaction, or at least the substantial part of said reaction is taking place during the thermocycling step. After the samples have been placed in the thermocycler, the samples are heated to first temperature between 90° C. and 100° C. This temperature transition period is thus sufficient to finalize the reverse transcriptase reaction step. This first heating as well as all subsequent heatings during the thermocycling protocol can take place at a rate of 10° C. per seconds. Preferably, the heating rate for the first heating step is 5° C. or per second or less.

Thus, the thermocycling step of the present invention can also be defined as comprising the steps of:
  increasing the temperature of the sample to a temperature between 90° C. and 100° C. at a temperature transition rate of 10° C. per second or less (preferably 5° C. per second or less) and
  decreasing the temperature of said sample to a second temperature between 50° C. and 75° C.

It is well understood by a person skilled in the art that various thermocycling protocols can be applied. In particular, a person skilled in the alt will be capable of optimizing the time intervals for holding the denaturation temperature between 90° C. and 100° C. and the second temperature between 50° C. and 75° C. Furthermore, in many cases one may select a three holding temperature cycle with a denaturation temperature, a primer annealing temperature between 50° C. and 60° C. and an extension temperature between 70° C. and 75° C. The method according to the present invention is applicable to all these different thermocycling protocols, provided that the thermocycling protocol starts with a denaturation characterized in that the temperature is first increased to a temperature between 90° C. and 100° C. at a transition rate of 10° C. per second or less.

In general, there are two different possibilities for selecting an appropriate enzyme system in order to perform the method according to the present invention. In a First alternative, the enzyme is a thermostable DNA polymerase which comprises both a DNA template-dependent DNA polymerase activity in order to perform the PCR part of the reaction and an RNA template-dependent DNA polymerase activity in order to perform the reverse transcriptase part of the one-step RT-PCR reaction. A variety of respective enzymes are known in the art. For example, the DNA polymerase of *Carboxydothermus hydrogenoformans* is capable of performing a one-step PCR (Roche Applied Science Catalog No. 12016338001). Preferably, the polymerases used are polymerases obtainable from organisms belonging to the eubacterial genus *Thermus*. In one preferred embodiment, the DNA polymerase of the *Thermus* species Z05 (U.S. Pat. No. 5,674,738) is used. In another highly preferred embodiment, the DNA polymerase of *Thermus thermophilus* (Roche Applied Science Catalog No. 11480014001) is used for a one-step RT-PCR method according to the present invention.

Alternatively, the one-step RT-PCR method according to the present invention is performed using an enzyme mixture comprising at least two DNA dependent polymerases. One polymerase is a DNA template-dependent thermostable DNA polymerase capable of performing a PCR reaction. The second enzyme is an RNA template-dependent DNA polymerase capable of performing the reverse transcriptase step of the one-step RT-PCR reaction. Such a reverse transcriptase according to the present invention does not need to be thermostable. For example, such a mixture may be composed of *Thermus aquaticus* polymerase and AMV reverse transcriptase (Roche Applied Science Catalog No. 11888382001).

In those cases where a preincubation step for initiation of the reverse transcriptase reaction is executed, the temperature for such a preincubation is between 20° C. and 65° C. Preferably, the temperature is between 37° C. and 65° C., preferably between 37° C. and 55° C. The selection of temperature primarily depends on two parameters, namely the choice of enzyme or enzymes and the tendency of the target RNA to form secondary structures. In case such tendency is very high, higher temperatures are preferred. In case thermostable DNA template-dependent polymerases comprising a reverse transcriptase activity are used, higher temperatures between 50° C. and 65° C. can be selected. In case, however, enzyme mixtures comprising a non thermostable reverse transcriptase are used, lower temperatures between 37° C. and 55° C. are applied.

In a specific particular embodiment of the invention, an RT-PCR for amplifying a target RNA comprises the steps of:
  providing a sample which is supposed to contain the target RNA.
  adding a reaction mixture comprising all reagents necessary to reverse transcribe said target RNA into cDNA and amplify at least a portion of said cDNA, said reaction mixture comprising *Thermus thermophilus* DNA polymerase,
  incubating said sample for a time of 5 seconds or less at a temperature between 37° C. and 65° C., and
  subjecting said sample to multiple cycles of a thermocycling protocol wherein the temperature of said cycle is varied between at least a first temperature between 90° C. and 100° C. and a second temperature between 50° C. and 75° C.

The method according to the present invention may be used for a variety of different qualitative and quantitative applications. In principle, any type of RNA may be transcribed and amplified. Most importantly, the method according to the present invention is applicable for amplifying and detecting mRNAs in a qualitative and quantitative manner. Thus, the present invention is also applicable for monitoring gene expression.

For the first strand cDNA synthesis, primers with an antisense sequence are used. These primers are either specific primers, oligo-dT primers which bind to the poly-A-rail of an mRNA, or random primers such as random hexamer primers. For subsequent PCR, a sequence specific primer in sense orientation is used as a forward primer. The reverse primer is a specific primer which may be identical to the specific primer used in the first strand cDNA synthesis reaction. Alternatively, the reverse primer may be a primer which hybridizes to a sequence located upstream from the binding side of the primer that has been used for the reverse transcriptase reaction.

The present invention is applicable for performing one-step RT-PCR of sequences of practically any amplicon Size up to 5 kb. For one-step RT-PCR reactions with a small product size of about 0.2 kb or less, no incubation step is required. For one-step RT-PCR reactions used in order to amplify sequences of more than 0.3 kb but less than 1 kb, an incubation step of about 20 seconds has been proven to be sufficient. For amplified targets above 1 kb, an incubation time of above 35 seconds to 42 seconds is advantageous.

A further important aspect of the present invention is a method of performing RT-PCR as disclosed above characterized in that the progress of said one-step RT-PCR reaction is monitored in real time. Different detection formats are known in the art. The below mentioned detection formats have been proven to be useful for 1-step RT-PCR and thus provide an easy and straight forward possibility for gene expression analysis:

a) TaqMan Hydrolysis Probe Format

A single-stranded hybridization probe is labeled with two components. When the first component is excited with light of a suitable wavelength, the absorbed energy is transferred to the second component, the so-called quencher, according to the principle of fluorescence resonance energy transfer (FRET). During the annealing step of the PCR reaction, the hybridization probe binds to the target DNA and is degraded by the 5'-3' exonuclease activity of the Taq polymerase during the subsequent elongation phase. As a result the excited fluorescent component and the quencher are spatially separated from one another and thus a fluorescence emission of the first component can be measured. TaqMan probe assays are disclosed in detail in U.S. Pat. No. 5,210,015, U.S. Pat. No. 5,538,848, and U.S. Pat. No. 5,487,972. TaqMan hybridization probes and reagent mixtures are disclosed is U.S. Pat. No. 5,804,375.

b) Molecular Beacons

These hybridization probes are also labeled with a first component and with a quencher, the labels preferably being located at both ends of the probe. As a result of the secondary structure of the probe, both components are in spatial vicinity in solution. After hybridization to the target nucleic acids, both components are separated from one another such that, after excitation with light of a suitable wavelength, the fluorescence emission of the first component can be measured (U.S. Pat. No. 5,118,801).

c) FRET Hybridization Probes

The FRET hybridization probe test format is especially useful for all kinds of homogeneous hybridization assays (Matthews, J. A., and Kricka, L. J., Analytical Biochemistry 169 (1988) 1-25). It is characterized by two single-stranded hybridization probes which are used simultaneously and are complementary to adjacent sites of the same strand of the amplified target nucleic acid. Both probes are labeled with different fluorescent components. When excited with light of a suitable wavelength, a first component transfers the absorbed energy to the second component according to the principle of fluorescence resonance energy transfer such that a fluorescence emission of the second component can be measured when both hybridization probes bind to adjacent positions of the target molecule to be detected. Alternatively to monitoring the increase in fluorescence of the FRET acceptor component, it is also possible to monitor fluorescence decrease of the FRET donor component as a quantitative measurement of a hybridization event.

In particular, the FRET hybridization probe format may be used in real time PCR in order to detect the amplified target DNA. Among all detection formats known in the art of real time PCR, the FRET hybridization probe format has been proven to be highly sensitive, exact, and reliable (WO 97/46707; WO 97/46712: WO 97/46714). As an alternative to the usage of two FRET hybridization probes, it is also possible to use a fluorescent-labeled primer and only one labeled oligonucleotide probe (Bernard, P. S. et al., Analytical Biochemistry 255 (1998) 101-107. In this regard, it may be chosen arbitrarily whether the primer is labeled with the FRET donor or the FRET acceptor compound.

d) SYBR Green (Molecular Probes, Inc.) Format

It is also within the scope of the invention if real time PCR is performed in the presence of an additive according to the invention in case the amplification product is detected using a double stranded nucleic acid binding moiety. For example, the respective amplification product can also be detected according to the invention by a fluorescent DNA binding dye which emits a corresponding fluorescence signal upon interaction with the double-stranded nucleic acid after excitation with light of a suitable wavelength. The dyes SYBR Green I and SYBR Gold have proven to be particularly suitable for this application. Intercalating dyes can alternatively be used. However, for this format, in order to discriminate the different amplification products, it is necessary to perform a respective melting curve analysis (U.S. Pat. No. 6,174,670).

The following examples and figures are provided to aid the understanding of the present invention, the true scope of which is set forth in the appended claims. It is understood that modifications can be made in the procedures set forth without departing from the spirit of the invention.

Example 1

For a real time one-step RT-PCR reaction, ABCC2 RNA (GenBank accession number U63970) was chosen as an amplification target. The sequence of the forward primer is located between positions 2728-2748, the sequence of the reverse primer is located between positions 2788-2807. Detection was performed according to the TaqMan hydrolysis probe principle (U.S. Pat. No. 5,804,375). The probe was labeled with FAM at the 5' end and TAMRA at the 3' end was derived from positions 2750-2780 from the ABCC2 RNA. (Langmann, T. et al., Clinical Chemistry 49 (2003) 230-238.

RT-PCR reactions were performed using the LIGHTCYCLER 480 (Roche Diagnostics GmbH) RNA Master Hydrolysis Probes from Roche Applied Science (Catalog No. 04991885001) in reaction volumes of 20 µl. This mastermix contains DNA polymerase from *Thermus thermophilus*.

Figure 1:
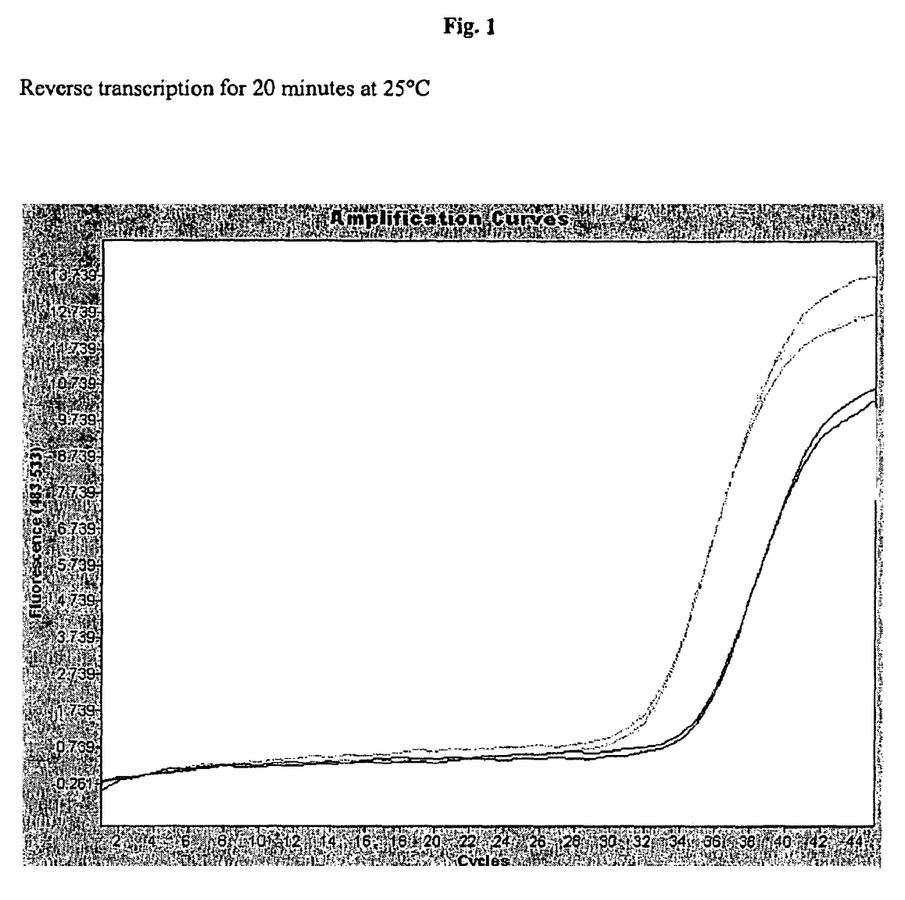
FIG. 1: Reverse transcription preincubation for 20 minutes at 25° C.
Figure 2:
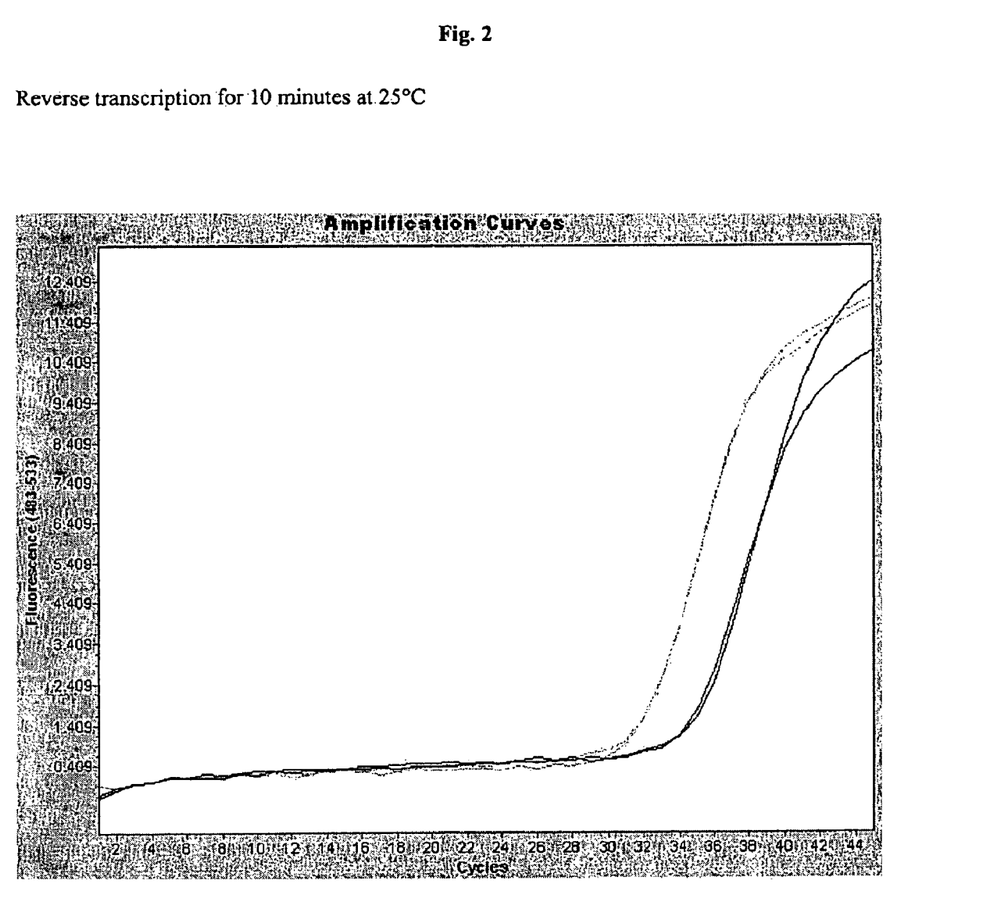
FIG. 2: Reverse transcription preincubation 10 minutes at 25° C.
Figure 3:
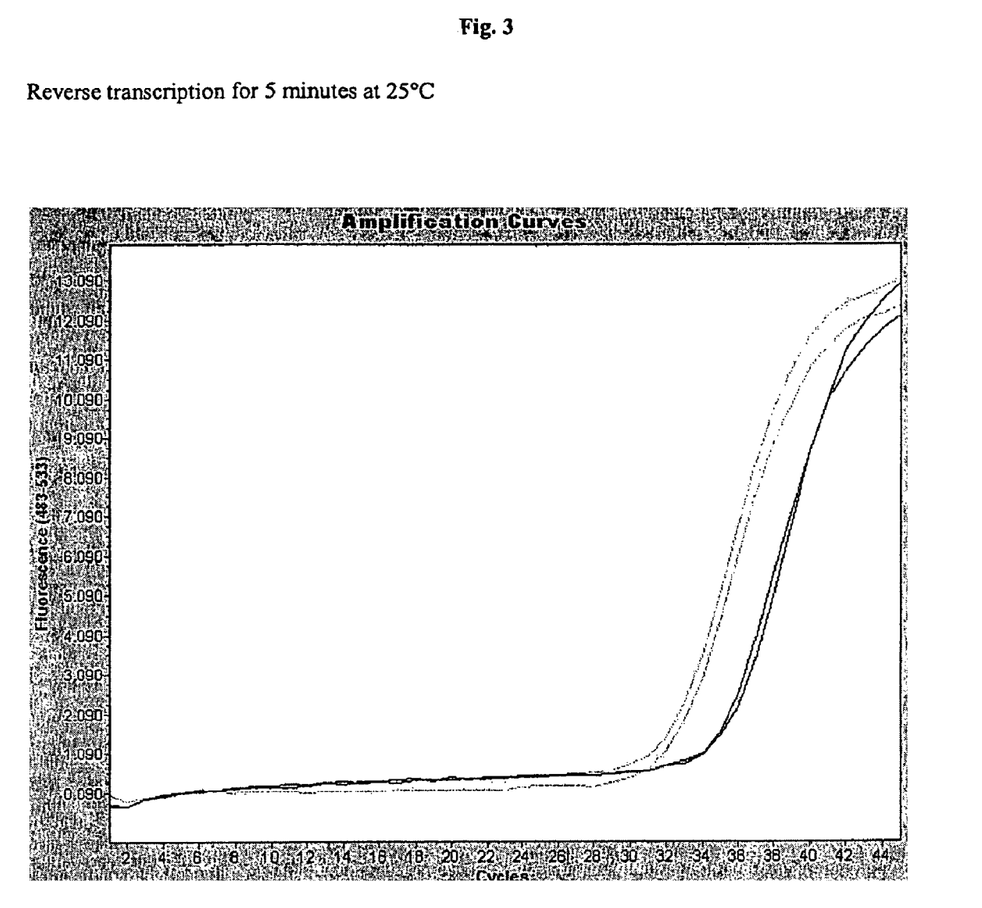
FIG. 3: Reverse transcription preincubation for 5 minutes at 25° C.
Figure 4:
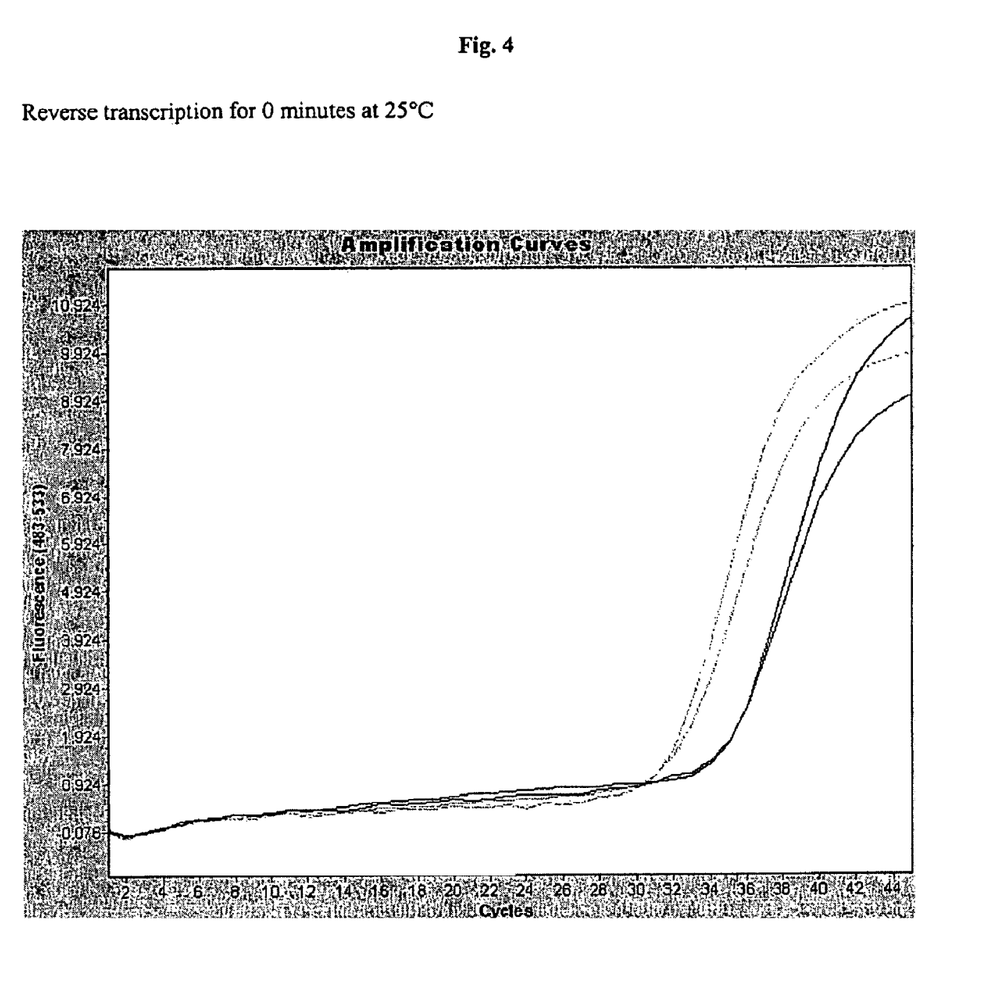
FIG. 4: Reverse transcription without preincubation

PCR setup was as follows:
100 pg or 10 pg of total RNA from human liver cells
7.4 µl RNA master
3.25 mM manganese acetate
0.5 µM of each primer
0.25 µM hydrolysis probe Reverse transcription was performed at 25° C. for 0 minutes, 5 minutes, 10 minutes, and 20 minutes in a LIGHTCYCLIER 480 (Roche Applied Science Catalog No. 04 640268001). PCR was performed with an initial denaturation for 30 seconds at 95° C., and 45 cycles with 95° C. for 15 seconds and 60° C. for 60 seconds. All heating rates were 4.8° C./s, whereas all cooling rates were 2.5° C./s. Amplification was monitored in real time. The results are shown in FIG. 1-4 as well as in the following Table 1.

TABLE 1

Crossing points of RT-PCR products generated with preincubation times and preincubation temperatures as indicated in the columns

| RNA concentration | 25° C./20 minutes | 25° C./10 minutes | 25° C./5 minutes | 25° C./0 minutes |
|---|---|---|---|---|
| 100 pg | 32.5 | 31.7 | 32.3 | 32.0 |
| 100 pg | 32.3 | 31.9 | 32.2 | 31.6 |
| 10 pg | 35.0 | 34.5 | 34.9 | 34.7 |
| 10 pg | 34.9 | 35.1 | 35.5 | 34.9 |

The crossing points indicate the cycle number at which fluorescent signaling exceeds a certain threshold level. Thus, the crossing points in this experiment are a measure for the sensitivity of the RT-PCR reaction under the different conditions disclosed. It can be seen from the table that similar or almost identical crossing points were obtained for RT-PCR of identical amounts of target RNA, independent from the time interval of preincubation at 25° C. Thus, a preincubation step for performing the reverse transcriptase reaction is not necessary.

Example 2

Figure 5:
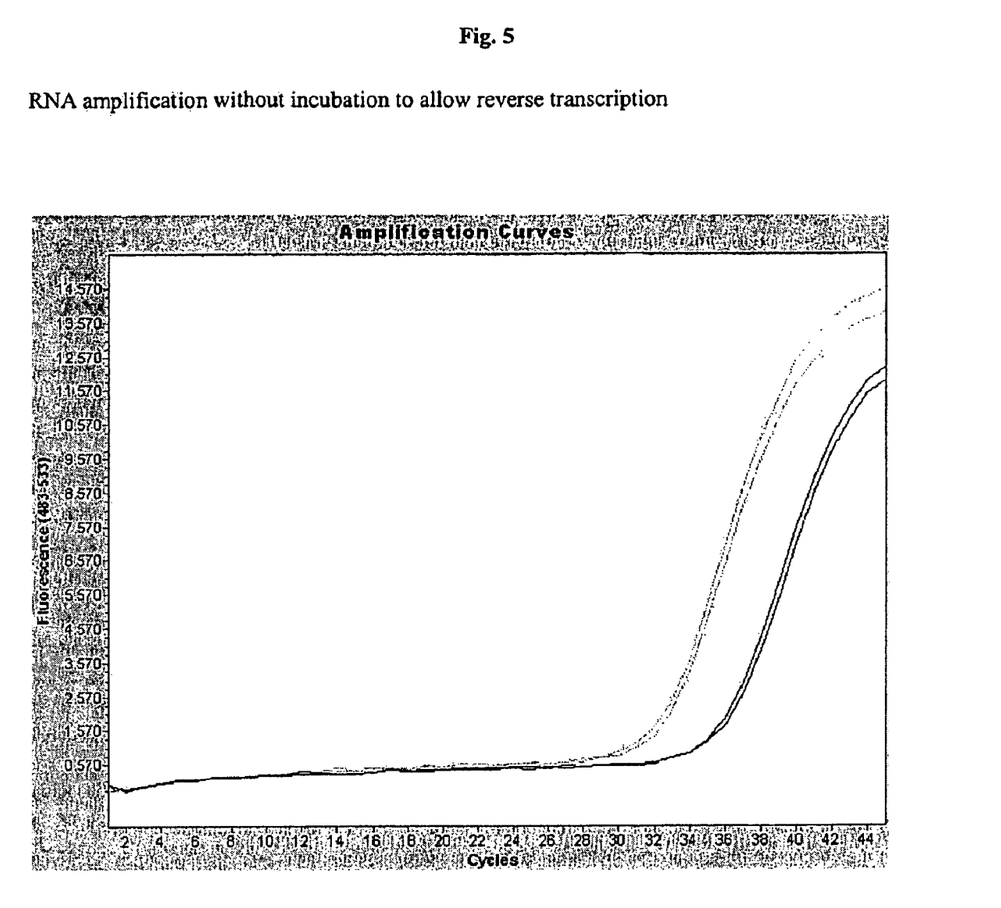
FIG. 5: RNA amplification without preincubation
Figure 6:
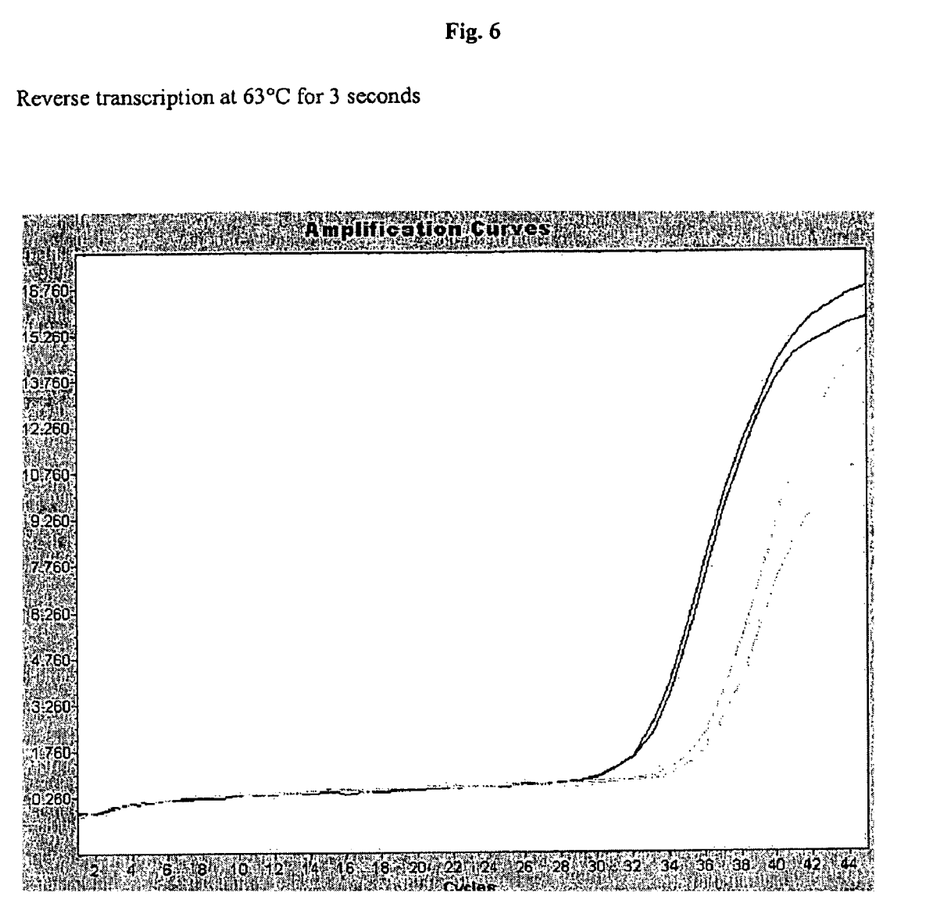
FIG. 6: Reverse transcription preincubation for 3 seconds at 63° C.
Figure 7:
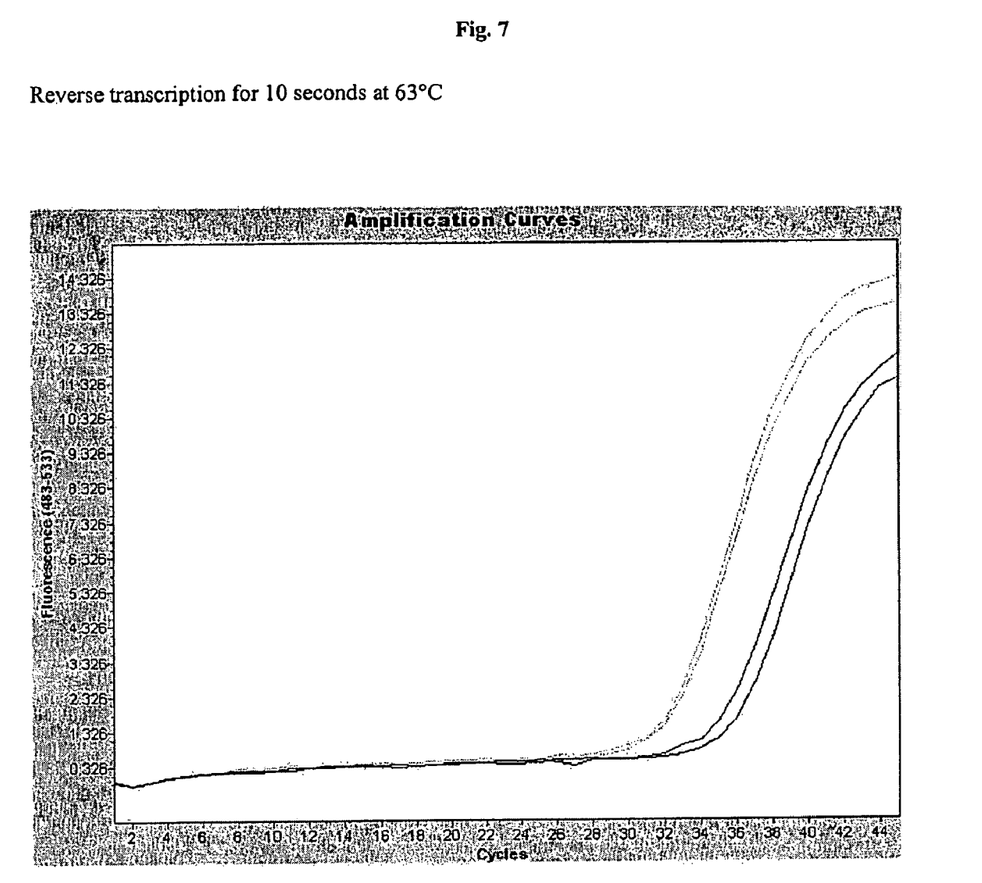
FIG. 7: Reverse, transcription preincubation for 10 seconds at 63° C.
Figure 8:
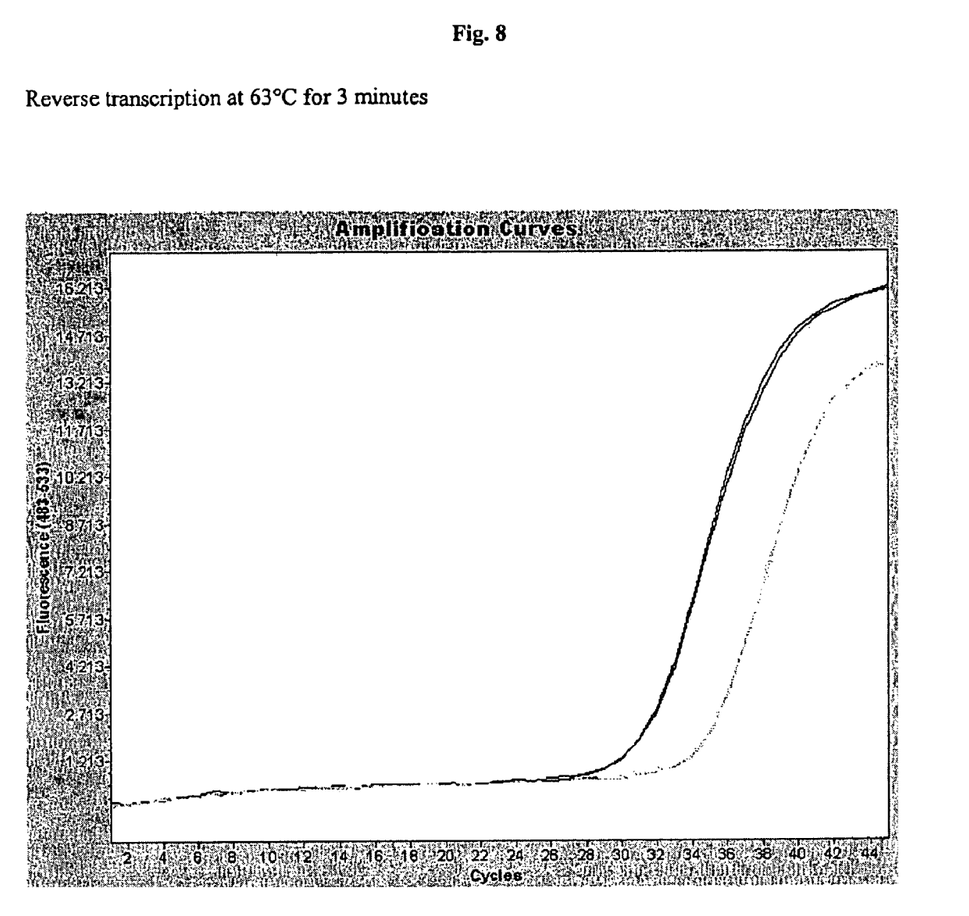
FIG. 8: Reverse transcription for three minutes at 63° C.

The complete experiment vas performed according to Example 1 with the exception that a preincubation step was performed at 63° C. for 0 seconds, 3 seconds, 10 seconds, or 3 minutes. The results are shown in FIG. 5-8 as well as in the following Table 2.

TABLE 2

Crossing points of RT-PCR products generated with preincubation times and preincubation temperatures as indicated in the columns

| RNA concentration | Directly into PCR | 63° C./3 seconds | 63° C./10 seconds | 63° C./3 minutes |
|---|---|---|---|---|
| 100 pg | 32.5 | 32.5 | 32.2 | 31.2 |
| 100 pg | 32.6 | 32.7 | 32.3 | 31.3 |
| 10 pg | 35.7 | 35.6 | 35.7 | 34.7 |
| 10 pg | 35.9 | 35.7 | 35.0 | 34.7 |

It can be seen from the table that similar and almost identical crossing points were obtained for RT-PCR of identical amounts of target RNA, independent from the time interval of preincubation at 63° C. Thus, a preincubation step for performing does not result in a better performance of the RT-PCR protocol.

Example 3

The complete experiment was performed according to Example 1 with the exceptions that (i) a mixture of 0.6 U AM-V reverse transcriptase and 0.4 U Taq DNA polymerase per reaction were used instead of Tth polymerase and (ii) the preincubation step was performed at 55° C. for 30 seconds, 50 seconds, or 10 minutes. The results are shown in the following Table 3.

TABLE 3

Crossing points of RT-PCR products generated with preincubation times and preincubation temperatures as indicated in the columns

| RNA concentration | 55° C./30 seconds | 55° C./50 seconds | 55° C./10 minutes |
|---|---|---|---|
| 1 ng | 32.3 | 31.6 | 32.0 |
| 1 ng | 32.3 | 31.7 | 31.9 |
| 100 pg | 35.1 | 34.8 | 33.8 |
| 100 pg | 34.8 | 34.2 | 34.2 |
| 10 pg | 36.7 | 36.1 | 35.8 |
| 10 pg | 36.2 | 36.1 | — |

What is claimed is:

1. A method for amplifying a target RNA comprising the steps of:
   providing a sample presumed to contain said target RNA,
   forming a mixture of said sample and reagents necessary to reverse transcribe said, target RNA into cDNA and amplify at least a portion of said cDNA,
   within 40 seconds or less of said forming, and
   subjecting said sample to multiple cycles of a thermocycling protocol wherein the temperature of said sample is varied between at least a first temperature between 90° C. and 100° C. and a second temperature between 50° C. and 75° C., thereby amplifying wherein the thermocycling protocol includes increasing the temperature of the sample to the first temperature at a rate of 10° C. per second or less.

2. The method of claim 1 wherein the temperature prior to said subjecting is between 37° C. and 55° C.

3. The method of claim 1 wherein the reagents for reverse transcription and amplification comprise a thermostable polymerase comprising DNA dependent polymerase activity and reverse transcriptase activity.

4. The method according to claim 3 wherein said polymerase is from *Thermus thermophilus*.

5. The method of claim 1 wherein the reagents for reverse transcription and amplification comprise a mixture of a thermostable polymerase comprising DNA dependent polymerase activity and at least a reverse transcriptase.

6. The method of claim 1 wherein said cDNA is shorter than 0.2 kb.

7. The method of claim 1 wherein progress of the amplification of said target RNA is monitored in real time.

* * * * *